United States Patent
Chang et al.

(10) Patent No.: US 9,886,757 B2
(45) Date of Patent: Feb. 6, 2018

(54) LESION DETECTING METHOD AND LESION DETECTING APPARATUS FOR BREAST IMAGE IN ROTATING MANNER

(71) Applicant: TAIHAO MEDICAL INC., Taipei (TW)

(72) Inventors: Ruey-Feng Chang, Taichung (TW); You-Wei Wang, New Taipei (TW); Rong-Tai Chen, Taichung (TW); Hong-Hao Chen, Hsinchu (TW); Jen-Feng Hsu, Taoyuan (TW); Hsin-Hung Lai, Taipei (TW)

(73) Assignee: TAIHAO MEDICAL INC., Taipei (TW)

(*) Notice: Subject to any disclaimer, the term of this patent is extended or adjusted under 35 U.S.C. 154(b) by 70 days.

(21) Appl. No.: 15/099,620

(22) Filed: Apr. 15, 2016

(65) Prior Publication Data
US 2017/0221199 A1 Aug. 3, 2017

(30) Foreign Application Priority Data
Jan. 28, 2016 (TW) .............................. 105102651 A

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/4312* (2013.01); *G06K 9/6202* (2013.01);
(Continued)

(58) Field of Classification Search
CPC ..... A61B 8/0825; A61B 8/483; A61B 5/4312; A61B 8/085; A61B 8/406; A61B 8/4483;
(Continued)

(56) References Cited

U.S. PATENT DOCUMENTS

| | | | |
|---|---|---|---|
| 4,015,836 A * | 4/1977 | Redington | A61B 6/04 5/601 |
| 8,824,762 B2 * | 9/2014 | Rivaz | A61B 8/485 382/131 |
| 2006/0241423 A1 | 10/2006 | Anderson et al. | |
| 2007/0081712 A1 | 4/2007 | Huang et al. | |
| 2008/0292164 A1 * | 11/2008 | Azar | A61B 5/0091 382/131 |
| 2009/0171244 A1 * | 7/2009 | Ning | A61B 6/032 600/567 |
| 2010/0074399 A1 * | 3/2010 | Majewski | G01T 1/00 378/37 |
| 2010/0185095 A1 | 7/2010 | Lin | |
| 2012/0189092 A1 * | 7/2012 | Jerebko | A61B 6/025 378/4 |
| 2013/0109963 A1 * | 5/2013 | Zhu | A61B 8/0825 600/427 |
| 2014/0018681 A1 | 1/2014 | Chang et al. | |

(Continued)

FOREIGN PATENT DOCUMENTS

| | | |
|---|---|---|
| CN | 1411356 | 4/2003 |
| CN | 101606853 | 12/2009 |

(Continued)

OTHER PUBLICATIONS

"Office Action of Taiwan Counterpart Application", dated Sep. 23, 2016, p. 1-p. 6, in which the listed references were cited.

*Primary Examiner* — Bhavesh Mehta
*Assistant Examiner* — Ian Lemieux
(74) *Attorney, Agent, or Firm* — JCIPRNET

(57) ABSTRACT

A lesion detecting method and a lesion detecting apparatus for breast image in a rotating manner are provided. In the method, a set of breast image in the rotating manner is obtained. The set of breast image in the rotating manner contains sub breast images. The sub breast image is reconstructed, to generate a reconstructed breast image. The reconstructed breast image is compared with the set of breast image in the rotating manner without being reconstructed. Accordingly, at least one lesion position would be confirmed according to the comparing result. Therefore, viewing a three-dimensional breast image would be convenient for medical staff, and false positive of detecting lesion would be reduced.

8 Claims, 8 Drawing Sheets

(51) Int. Cl.
  *A61B 5/00* (2006.01)
  *G06K 9/62* (2006.01)
  *G06T 11/00* (2006.01)
  *A61B 6/02* (2006.01)
  *A61B 8/08* (2006.01)
  *A61B 5/055* (2006.01)

(52) U.S. Cl.
  CPC .......... *G06T 7/0044* (2013.01); *G06T 7/0081* (2013.01); *G06T 11/006* (2013.01); *A61B 5/055* (2013.01); *A61B 6/025* (2013.01); *A61B 8/0825* (2013.01); *A61B 2576/02* (2013.01); *G06T 2207/10016* (2013.01); *G06T 2207/30068* (2013.01); *G06T 2207/30096* (2013.01)

(58) Field of Classification Search
  CPC .................. A61B 8/463; A61B 8/5223; G06T 2207/30068; G06T 7/0012; G06T 11/006; G06T 2207/10016; G06T 2207/10136; G06T 2207/30096; G06T 7/0044; G06T 7/0081
  See application file for complete search history.

(56) References Cited

U.S. PATENT DOCUMENTS

| | | | | |
|---|---|---|---|---|
| 2014/0357998 | A1* | 12/2014 | Suzuki | A61B 5/708 600/440 |
| 2015/0228092 | A1* | 8/2015 | Claus | G06T 11/006 382/131 |
| 2016/0310036 | A1* | 10/2016 | Endo | A61B 5/0037 |
| 2016/0314582 | A1* | 10/2016 | Endo | A61B 5/0037 |

FOREIGN PATENT DOCUMENTS

| | | |
|---|---|---|
| TW | M448263 | 3/2013 |
| TW | 201347737 | 12/2013 |
| TW | M521447 | 5/2016 |

* cited by examiner

LESION DETECTING METHOD AND LESION DETECTING APPARATUS FOR BREAST IMAGE IN ROTATING MANNER

CROSS-REFERENCE TO RELATED APPLICATION

This application claims the priority benefit of Taiwan application serial no. 105102651, filed on Jan. 28, 2016. The entirety of the above-mentioned patent application is hereby incorporated by reference herein and made a part of this specification.

BACKGROUND OF THE DISCLOSURE

Field of the Disclosure

The disclosure relates to a medical image processing technique, and particularly relates to a lesion detecting method and a lesion detecting apparatus for breast image in rotating manner.

Description of Related Art

Mammary carcinoma is one of the most common malignant tumors in woman, and the main symptoms thereof include breast tumor, abnormal secretions, or shape variation, etc. To early screen the abnormal breast symptoms avails treating the tumor as early as possible, so as to decrease a chance of deterioration or proliferation of cancer cells. Screening methods such as clinical or self breast detection, biopsy, mammography, ultrasound or magnetic resonance imaging, etc., have been widely used in clinical practice or become important issues in academic researches.

According to researches, it is known that compared to a low density breast, women with a high density breast has a high risk of suffering from breast cancer. Therefore, density analysis on breast and mammary glandular tissues is also an important factor in breast cancer assessment. On the other hand, although a computer aided detection (CADe) system has been used in clinical practice to automatically identify tumors, bumps or calcifications, it still has a high risk of false positive.

SUMMARY OF THE DISCLOSURE

The disclosure is directed to a lesion detecting method and a lesion detecting apparatus for breast image in a rotating manner, which efficiently reduces false positive of a computer aided detection system.

The disclosure provides a lesion detecting method for breast image in a rotating manner, which at least (but not limited to) following steps. A set of breast image in the rotating manner is obtained. The set of breast mage in the rotating manner contains a plurality of sub breast images. The sub breast images are reconstructed to generate a reconstructed breast image. The reconstructed breast image is compared with the set of breast image in the rotating manner without being reconstructed to confirm at least one lesion position.

According to another aspect, the disclosure provides a lesion detecting apparatus, which at least includes (but not limited to) a storage unit and a processing unit. The storage unit records a plurality of modules. The processing unit is coupled to the storage unit, and accesses and executes the modules recorded in the storage unit. The modules include an image input module, an image reconstruction module and a lesion determination module. The image input module obtains a set of breast image in the rotating manner. The set of breast image in the rotating manner contains a plurality of sub breast images. The image reconstruction module reconstructs the sub breast images to generate a reconstructed breast image. The lesion determination module compares the reconstructed breast image with the set of breast image in the rotating manner without being reconstructed. Accordingly, the lesion determination module may confirm at least one lesion position according to the comparing result.

According to the above description, in the lesion detecting method and the lesion detecting apparatus for breast image in a rotating manner provided by the embodiments of the disclosure, the breast image in the rotating manner is reconstructed, and the reconstructed breast image is compared with the breast image in the rotating marinerto confirm a lesion (for example, tumor, bump or calcification) position. In this way, the embodiments of the disclosure assist reducing false positive of the computer aided detection system.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification The drawings illustrate embodiments of the disclosure and, together with the description, serve to explain the principles of the disclosure.

DESCRIPTION OF EMBODIMENTS

Figure 1:
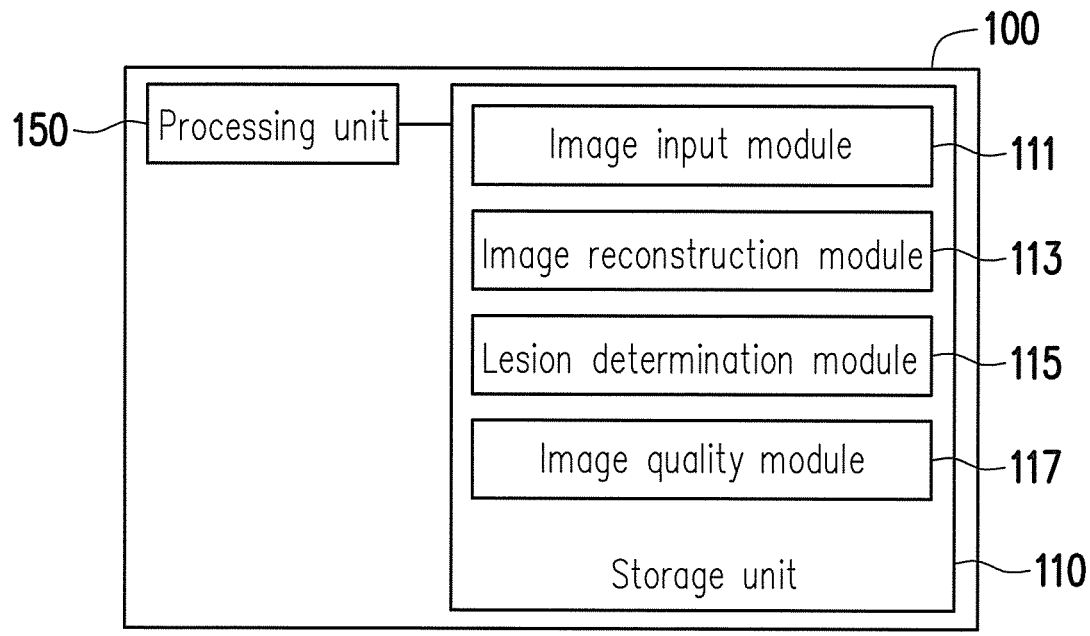
FIG. 1 is a block diagram of a lesion detecting apparatus according to an embodiment of the disclosure.

FIG. 1 is a block diagram of a lesion detecting apparatus according to an embodiment of the disclosure. Referring to FIG. 1, the lesion detecting apparatus 100 at least includes (but not limited to) a storage unit 110 and a processing unit 150. The lesion detecting apparatus 100 can be an electronic apparatus such as a server, a user device, a desktop computer, a notebook, a network computer, a working station, a personal digital assistant (PDA), a personal computer (PC), a computer aided detection (CADe) system, etc., which is not limited by the disclosure.

The storage unit 110 can be any type of a fixed or movable random access memory (RAM), a read-only memory (ROM), a flash memory or a similar device or a combination of the aforementioned devices. In the present embodiment, the storage unit 110 is used for storing a breast image in a rotating manner, sub breast images, a reconstructed breast image, scanning parameters, a program code, a device configuration, buffer or permanent data, and records software programs such as an image input module 111, an image reconstruction module 113, a lesion determination module 115, and an image quality module 117. Operation details of the above modules are described later in following embodiments. The storage unit 110 of the present embodiment is not limited to be a single memory device, and the aforementioned software modules can also be separately stored in two or more memory devices of the same type or different types.

Functions of the processing unit 150 can be implemented by using a programmable unit such as a central processing unit (CPU), a microprocessor, a micro controller, a digital signal processing (DSP) chip, a field programmable gate array (FPGA), etc. The functions of the processing unit 150 can be implemented by using an independent electronic device or integrated circuit (IC), and the processing unit 150 can also be implemented in a hardware or software manner.

Figure 2:
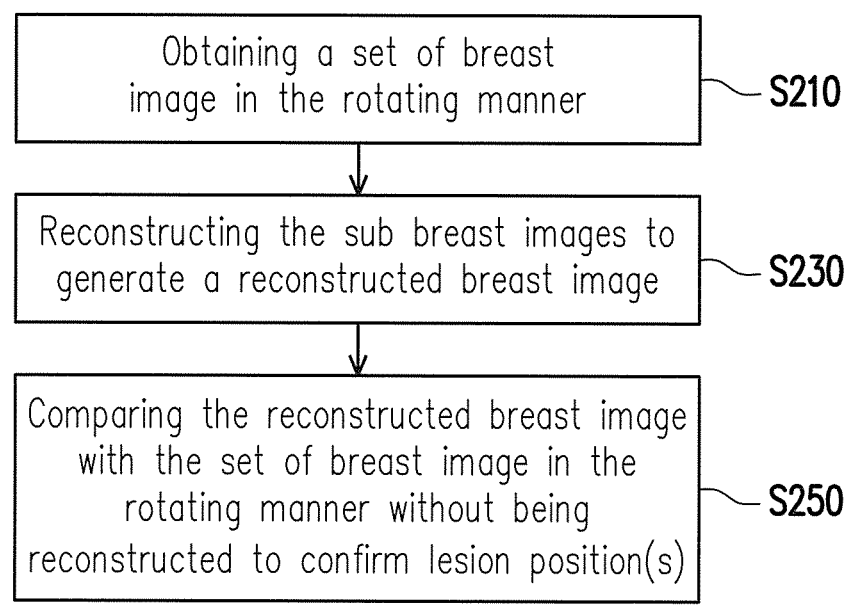
FIG. 2 is a flowchart illustrating a lesion detecting method for breast image in a rotating manner according to an embodiment of the disclosure.

In order to facilitate understanding an operation flow of the embodiment of the disclosure, a plurality of embodiments is provided below to describe a flow that the lesion detecting apparatus 100 of the present embodiment performs breast image processing and lesion detection in detail. FIG. 2 is a flowchart illustrating a lesion detecting method for breast image in a rotating manner according to an embodiment of the disclosure. Referring to FIG. 2, the method of the present embodiment is adapted to the lesion detecting apparatus 100 of FIG. 1. The method of the present embodiment is described below with reference of various components and modules of the lesion detecting apparatus 100. Various steps of the method can be adjusted according to an actual implementation requirement, which is not limited by the disclosure.

In step S210, the image input module 111 obtains a set of breast image in the rotating manner. The set of breast image in the rotating manner contains a plurality of (or at least one slice of) sub breast images. In the present embodiment, the sub breast images are respectively obtained through a scanner by circling under a breast image taking container for one circle to implement rotatory scanning. The scanner, for example, has a probe based on a medical image scanning technique such as automated breast ultrasound (ABUS), digital breast tomosynthesis (DBT), magnetic resonance imaging. (MRI), etc. Regarding the ultrasound scanning, the breast image taking container can be loaded with liquid or water-soluble ointment to serve as ultrasonic transmission media.

Figure 3:
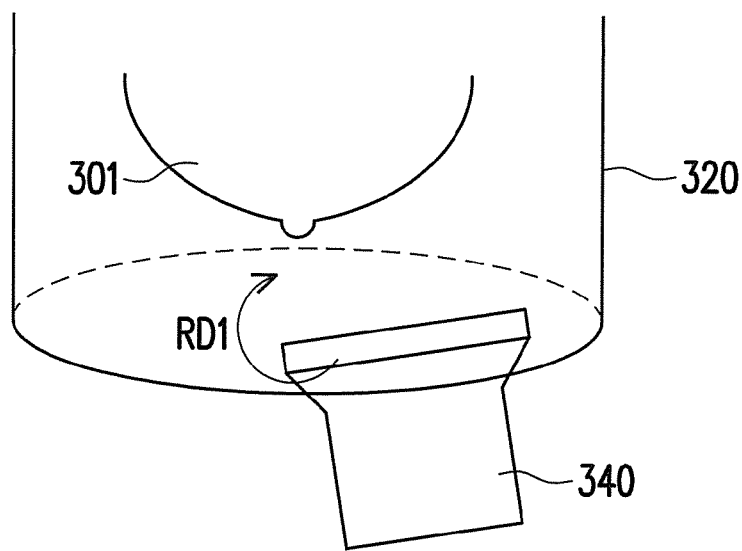
FIG. 3 is an example of rotatory scanning.

For example, FIG. 3 is an example of rotatory scanning. Referring to FIG. 3, a breast 301 of a user can be completely or partially disposed in a cylindrical breast image taking container 320 as the user lays down in a prone position. A movable scanner 340 with probe(s) is disposed under the bottom of the (fixed) cylindrical breast image taking container 320, and a mechanical device (not shown) can be used to drive the scanner 340 to rotate by at least one circle (360°) along a rotation direction RD1 (i.e. clockwise) or a direction opposite to the rotation direction RD1 (i.e. anticlockwise), such that a scanning range may cover all of or a part of a projection area of the breast 301. During the scanning process, the scanner 340 scans the breast 301 to obtain one sub breast image by every rotation angle (for example, 3°, 5°, 8°, etc.). For example, the rotation angle is 3°, and the scanner 340 rotates by one circle) 360°) to obtain 120 sub breast images.

It should be noted that before the rotatory scanning is performed, scanning parameters can be preset or manually adjusted. The scanning parameters at least include (but not limited to) an image scanning start position, a rotation direction (clockwise or anticlockwise), a rotation angle, etc., and can be recorded in the storage unit 110 for subsequent use.

The image input module 111 may obtain the breast image in the rotating manner from the storage unit 110, through a wireless or wired communication unit (for example, Wi-Fi, Ethernet), directly through a medical image scanner (for example, an ABUS scanner, a MRI scanner, etc.) of FIG. 3, or from a storage device (for example, a DVD, a flash drive, a hard disk, etc.).

In step S230, the image reconstruction module 113 reconstructs the sub breast images to generate a reconstructed breast image. In order to facilitate viewing the breast image obtained through the rotating manner according to different viewing angles, in the embodiment of the disclosure, the reconstruction is performed according to rotation characteristics of the rotatory scanning.

In an embodiment, the image reconstruction module 113 transforms the sub breast images into an image set according to the scanning start position, the rotation angle and the rotation direction of the scanner, and determines a missing position of each gap between two adjacent sub breast images in the image set, and complement the mission position through an interpolation method.

Figure 4:
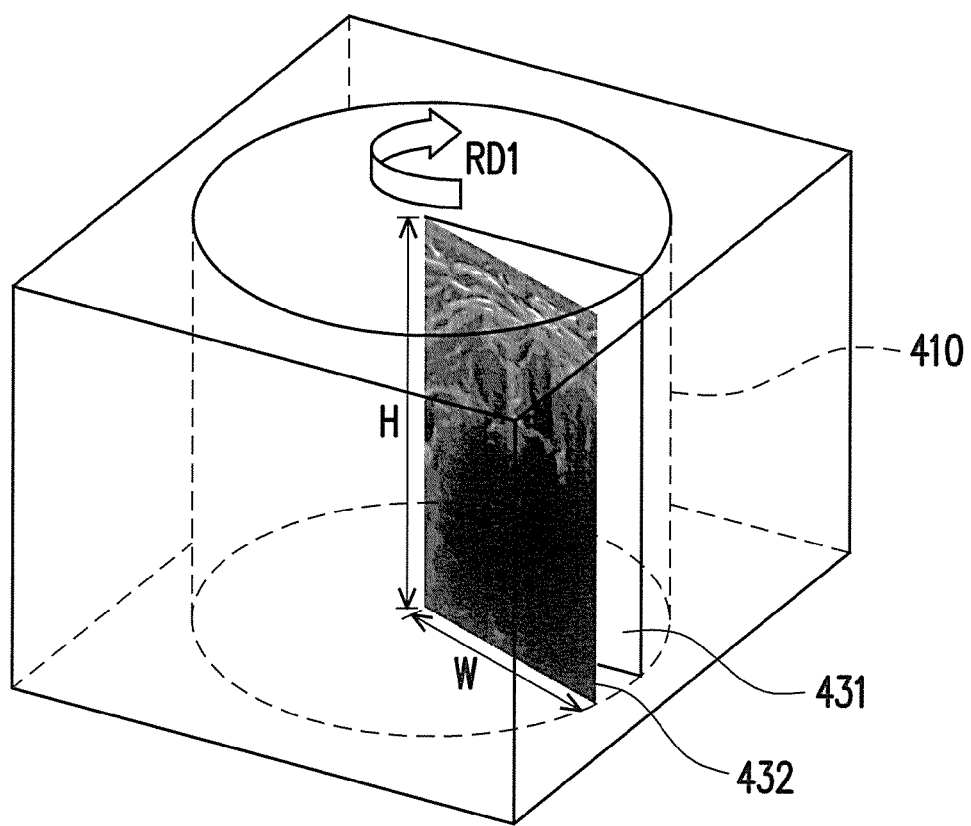
FIG. 4 is a schematic diagram of a breast image in the rotating manner in a three-dimensional space.

To be specific, FIG. 4 is a schematic diagram of a breast image in the rotating manner in a three-dimensional space. For simplicity's sake, only two sub breast images 431 and 432 in FIG. 4 are taken as an example for description, though the disclosure is not limited thereto. A width W of each sub breast image is a rotation radius (for example, a length that the scanner 340 of FIG. 3 can scan one time), and a height H thereof is a maximum depth that can be scanned by the scanner. The image reconstruction module 113 sequentially arranges each of the sub breast images (for example, the sub breast images 431 and 432) obtained through one circle of the rotatory scanning in the respective scanning positions according to the recorded or predetermined scanning parameters (for example, the image scanning start position, the clockwise or anticlockwise rotation, the rotation angle, etc.), so as to form a cylinder 410. Now, in the cylinder 410, the two sub breast images 431 and 432 have a gap (i.e. do not have pixels or scanning images) there between.

Figure 5A:
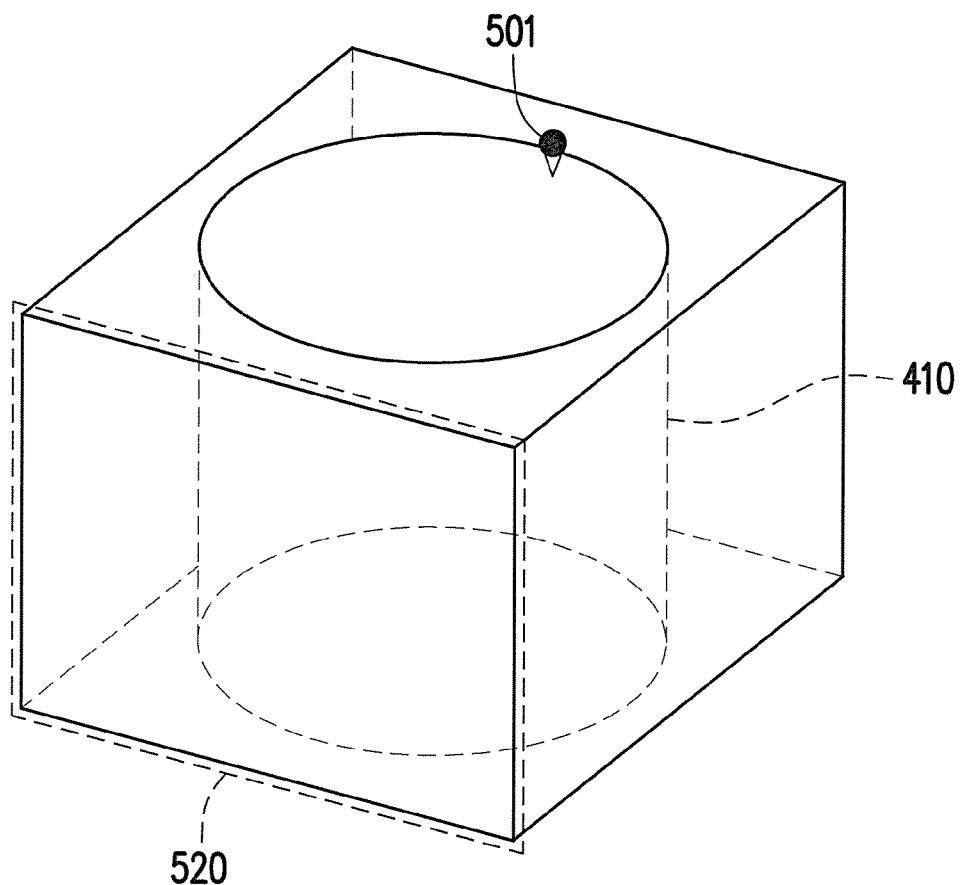
FIG. 5A-FIG. 5C are schematic diagrams of a fill-up operation according to an embodiment of the disclosure.
Figure 5B:
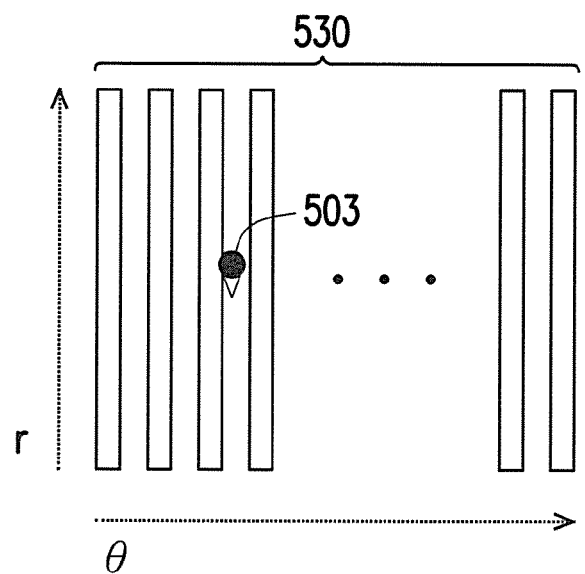
Figure 5C:
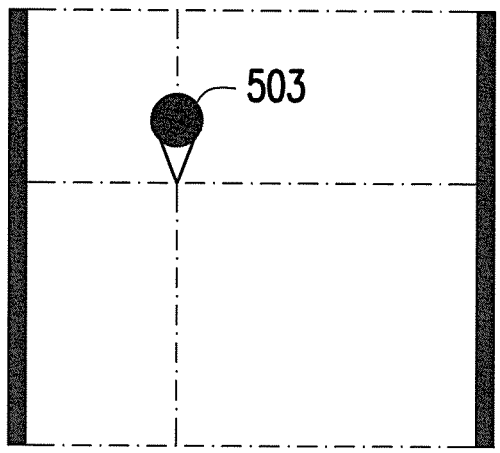

Then, the image reconstruction module 113 performs an operation to fill up the gaps. FIG. 5A-FIG. 5C are schematic diagrams of a fill-up operation according to an embodiment of the disclosure. Referring to FIG. 5A, the image reconstruction module 113 establishes a two-dimensional (2D) Cartesian coordinate system for the cylinder 410 formed by a plurality of the sub breast images in FIG. 4. For example, the 2D Cartesian coordinate system of a plane where the round top of the cylinder 410 is located.

The image reconstruction module 113 may transform the 2D Cartesian coordinate system into a coordinate system represented by a rotation angle and a radius length. To be specific, coordinates of a separation position 501 of two adjacent sub breast images in the Cartesian coordinate system are defined as (x1, y2) (a center point of the round top of the cylinder 410 is taken as an origin (0,0) and a connection line of the image scanning start position and the center point of the round top is an x-axis (or referred to as a horizontal axis)), and a diameter width Width (i.e. 2*W) of the round top of the cylinder 410 and a height Height (i.e. H) are defined. Then, the image reconstruction module 113 transforms the coordinates (x1, y1) according to following equations (1) (Pythagorean theorem) and (2) to obtain coordinates (r1, θ1):

$$r1 = \sqrt{\left(x1 - \frac{Width}{2}\right)^2 + \left(y1 - \frac{Width}{2}\right)^2} \quad (1)$$

$$\theta1 = \tan^{-1}\left(\frac{\left(y1 - \frac{Width}{2}\right)}{\left(x1 - \frac{Width}{2}\right)}\right) \quad (2)$$

Where, r1 represents a distance between the position and the center point of the round top of the cylinder 410, and θ1 represents a rotation angle started from the scanning start position.

According to the aforementioned transformation, the image reconstruction module 113 maps a part of or all of the sub breast images to the image set. Referring to FIG. 5B, a horizontal axis of such coordinate system is rotation angle θ (started from the scanning start position), and a vertical axis is the radius r. The sub breast images are sequentially arranged on the r-θ coordinate system along the rotation direction, and are reconstructed to form an image set 530. For example, if the rotation direction RD1 in FIG. 4 is clockwise, the sub breast image 431 in the image set is then located to the left of the sub breast image 432. The separation position 501 in FIG. 5A can also be mapped to a missing position 503 in the image set 530.

FIG. 5C is partial enlarged view of the image set 530. The image reconstruction module 113 can complement the mission position 503 through bilinear interpolation, bicubic interpolation, nearest interpolation, etc. After the gaps of all of the adjacent sub breast images are complemented, the integral image set (for example, without missing position) is formed. The image reconstruction module 113 may transform the image set from the r-θ coordinate system back to the presentation of FIG. 5A to form a 3D reconstructed breast image. The reconstructed breast image does not have the gap between two adjacent sub breast images shown in FIG. 4.

The processing unit 150 may further display the reconstructed breast image through a display unit (not shown, for example, a liquid crystal display (LCD), a plasma display panel (PDP), an organic light emitting diode (OLED), etc.), and may receive an input operation of the user through an input unit (not shown, for example, a touch device, a keyboard, a mouse, etc.), so as to inspect the reconstructed breast image via different viewing angles.

In step S250, the lesion determination module 115 compares the reconstructed breast image with the set of breast image in the rotating manner without being reconstructed to confirm at least one lesion position. In the present embodiment, a region-based lesion (for example, tumor, bump or calcification, etc.) detecting method is used to automatically detect the breast image in the rotating manner. According to the provided regional screening method, the suspicious lesion region is conditionally screened to find out the lesion position.

Figure 6:
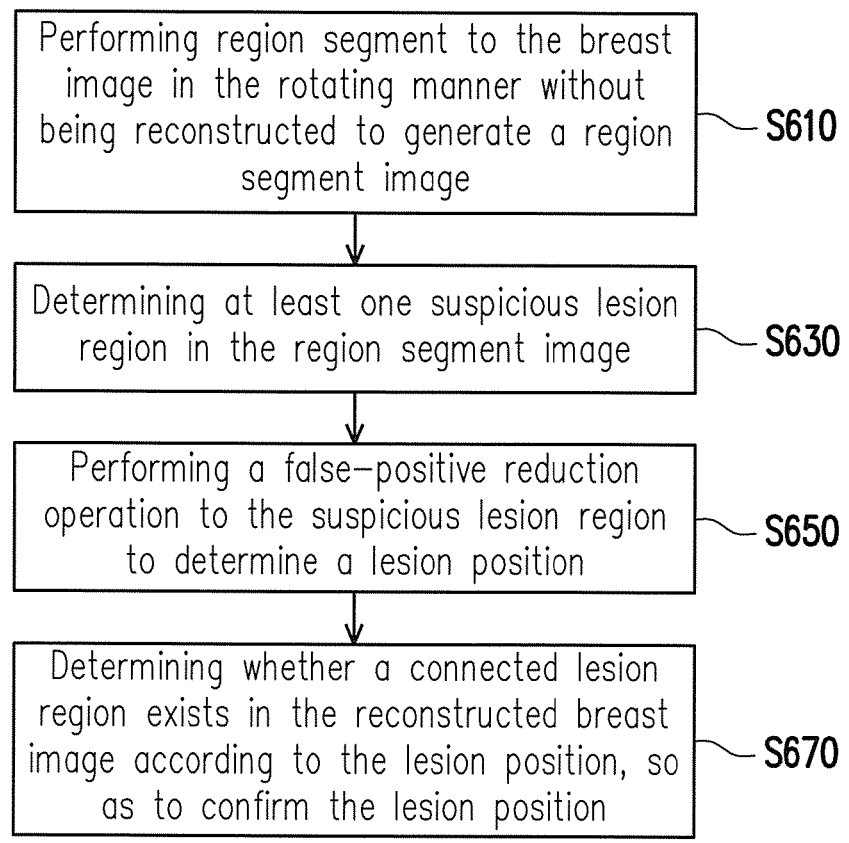
FIG. 6 is a flowchart illustrating an automatic lesion detecting method according to an embodiment of the disclosure.

FIG. 6 is a flowchart illustrating an automatic lesion detecting method according to an embodiment of the disclosure. Referring to FIG. 6, in step S610, the lesion determination module 115 performs region segment to the breast image in the rotating manner without being reconstructed to generate a region segment image. The lesion determination module 115 may use an original image (i.e. a slice of sub breast image in the breast image in the rotating manner without being reconstructed) to perform pixel-based or texture difference-based region segment (for example, watershed segment, Markov random field (MRF) segment).

Figure 7A:
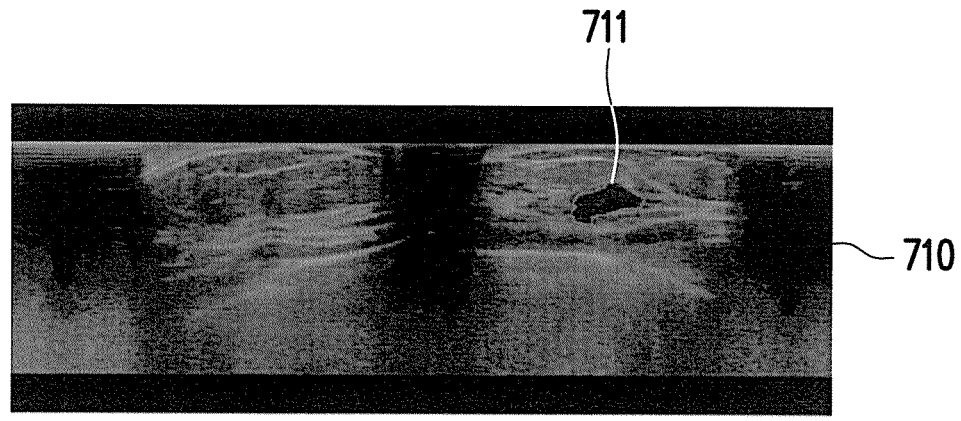
FIG. 7A is a partial image of a breast image in the rotating manner without being reconstructed.
Figure 7B:
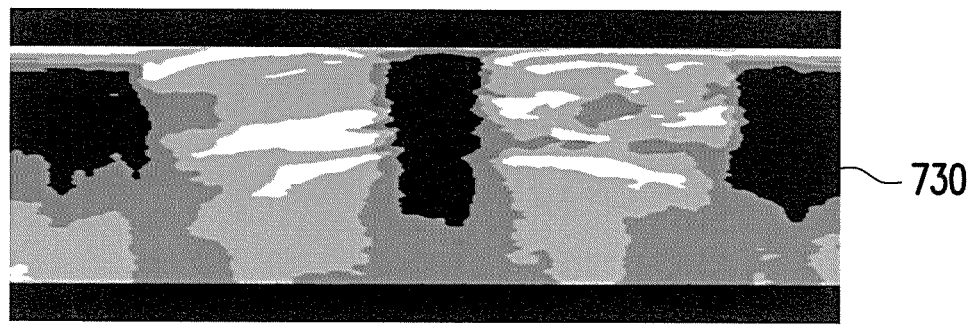
FIG. 7B shows a region segment image.

For example, FIG. 7A is a partial image of the breast image in the rotating manner without being reconstructed. It is assumed that the breast image in the rotating manner 710 has a tumor 711. After the lesion determination module 115 performs the region segment to the breast image in the rotating manner 710, a region segment image 730 shown in FIG. 7B is produced. In the region segment image 730, the pixels having the same or similar texture characteristics are divided into a same region (indicated by a same color). It should be noted that various parameters in the region segment algorithm can be adjusted according to an actual requirement, which is not limited by the disclosure.

Figure 7C:
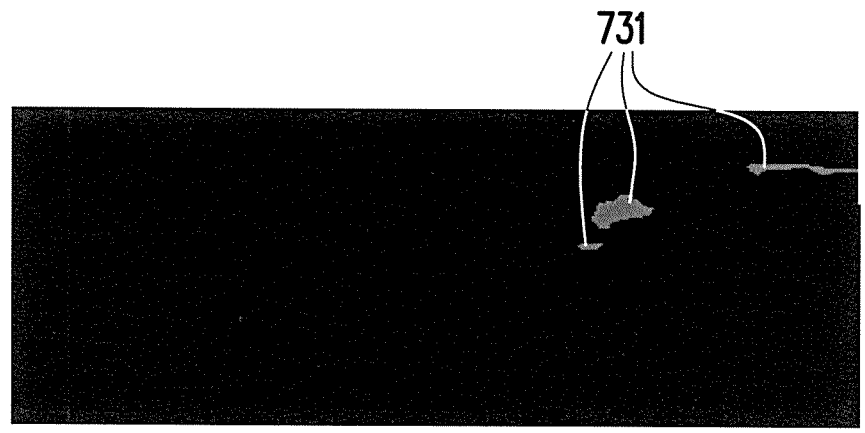
FIG. 7C shows a suspicious lesion region determined according to the region segment image of FIG. 7B.

In step S630, the lesion determination module 115 determines at least one suspicious lesion region in the region segment image. To be specific, after the lesion determination module 115 segments the breast image in the rotating manner, the region segment image still includes a plenty of unnecessary blocks, and the target lesion block is also included therein. The lesion determination module 115 may perform preliminary screening according to a target characteristic (for example, a darker region, an approximate ellipse, a long-short axis ratio) to be detected by using pixel characteristics of each block (for example, an average value, the maximum value, the minimum value, a median value, a variance, etc.), so as to determine the suspicious lesion region(s), where the characteristics and features of each block of the image can be adjusted according to an actual requirement. For example, FIG. 7C shows a suspicious lesion region 731 determined according to the region segment image 730 of FIG. 7B.

Figure 7D:
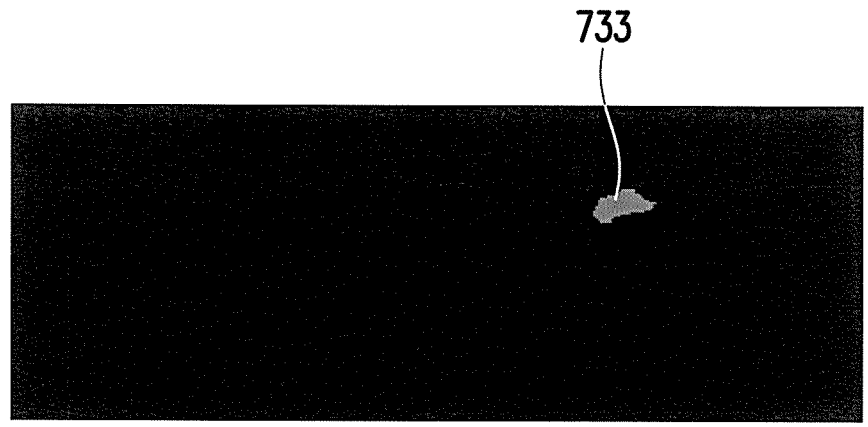
FIG. 7D shows a lesion position of FIG. 7C screened through the false-positive reduction operation.

In step S650, the lesion determination module 115 may perform a false-positive reduction operation to the suspicious lesion region to determine a lesion position. To be specific, after the preliminary screening, the lesion determination module 115 further performs false-positive reduction on the remained blocks by using the screened suspicious lesion blocks. The characteristics used by the false-positive reduction may at least include (but not limited to) three parts: shape (for example, an area, a long-short axis ratio), pixel strength (for example, an average value, a standard deviation) and texture (for example, gray-level co-occurrence matrix (GLCM), Markov random field (MRF), or Gabor filter). In other words, the lesion determination module 115 may screen the remained blocks according to the predetermined characteristics or manually selected characteristics to find out the target lesion position(s). For example, FIG. 7D shows a lesion position 733 of FIG. 7C screened through the false-positive reduction operation.

In step S670, the lesion determination module 115 determines whether a connected lesion region exists in the reconstructed breast image according to the lesion position, so as to confirm the lesion position(s). To be specific, the lesion determination module 115 compares the determined lesion position (for example, the lesion position 733 in FIG. 7D) with the 3D reconstructed breast image. If the 3D reconstructed breast image has the connected lesion region (i.e. a region corresponding to the lesion position), it represents that the lesion actually exists (or an existence chance thereof is higher than 80%, 90%, etc.) If he 3D reconstructed breast image does not have the connected lesion region, it represents that the lesion does not exist (or the existence chance thereof is lower than 10%, 15%, etc.).

In some embodiments, the processing unit 150 may further present one of prompt massages of finding lesion (for example, "find tumor!"), the lesion position, the suspicious lesion region, the lesion region, etc., or a combination thereof through the display unit, so as to assist the medical staff to clearly learn the inspection situation.

Moreover, in order to maintain quality control of the image scanning, in some embodiments, the image quality module 117 further determines whether the breast image in the rotating manner is complete or a shooting error thereof is too high (for example, an error rate is greater than 70%, 80%, etc.). The image quality module 117 may perform a vertical projection on an image of a partial thickness region in the breast image in the rotating manner to generate a projection image, and determines the image quality of the breast image in the rotating manner according to a ratio between a shooting error type and a skin tissue type in the projection image.

To be specific, after the step S210 or S230 or before the step S250, the processing unit 150 determines whether to perform subsequent lesion detection according to a result of the image quality determined by the image quality module 117. The image quality module 117 may determine the thickness region of different thickness value (for example, 2 cm, 5 cm, etc., which is varied along with different users) according to the 3D reconstructed breast image or the sub breast image set forming the cylinder 410 of FIG. 4.

Figure 8:
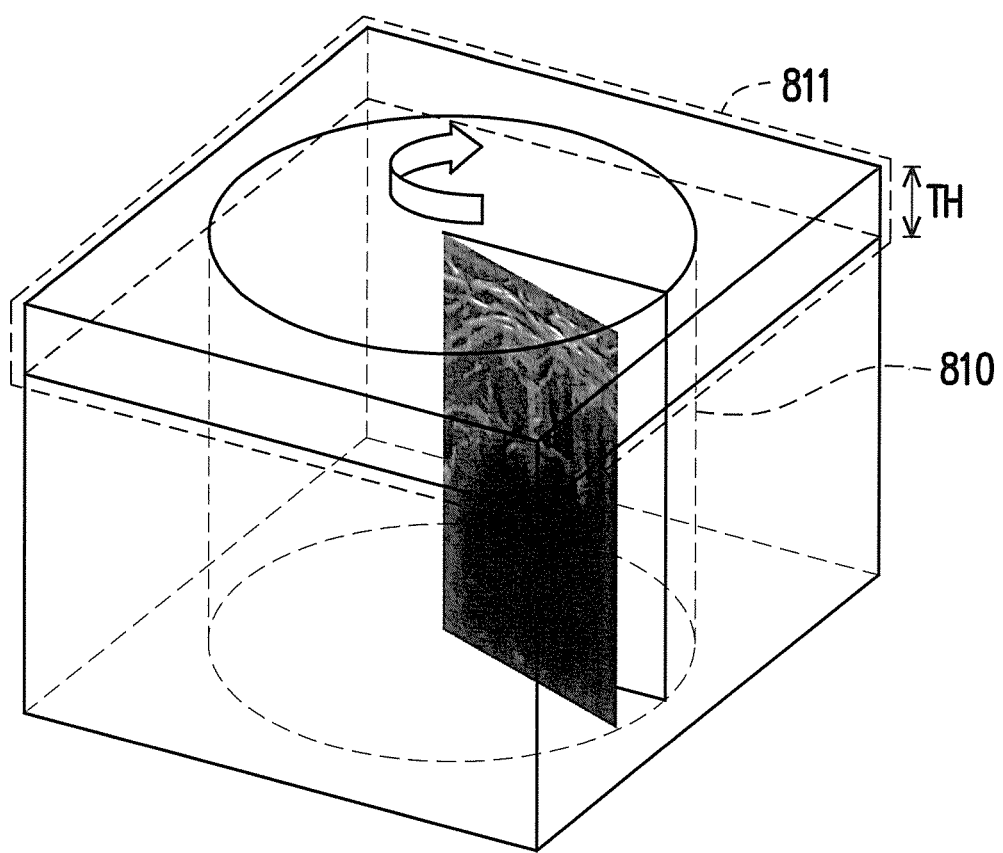
FIG. 8 is a schematic diagram of determining a thickness region.

For example, FIG. 8 is a schematic diagram of determining the thickness region. The image quality module 117 determines a thickness value TH according to a top part of the sub breast image set forming the cylinder 810 or the reconstructed breast image, so as to determine a thickness region 811.

The image quality module 117 then performs the vertical projection on the image of the determined thickness region (for example, the thickness region 811 of FIG. 8), where the lowest pixel value of all of the pixels along the vertical direction in each of the positions can be taken as a value of each of the aforementioned positions.

Figure 9A:
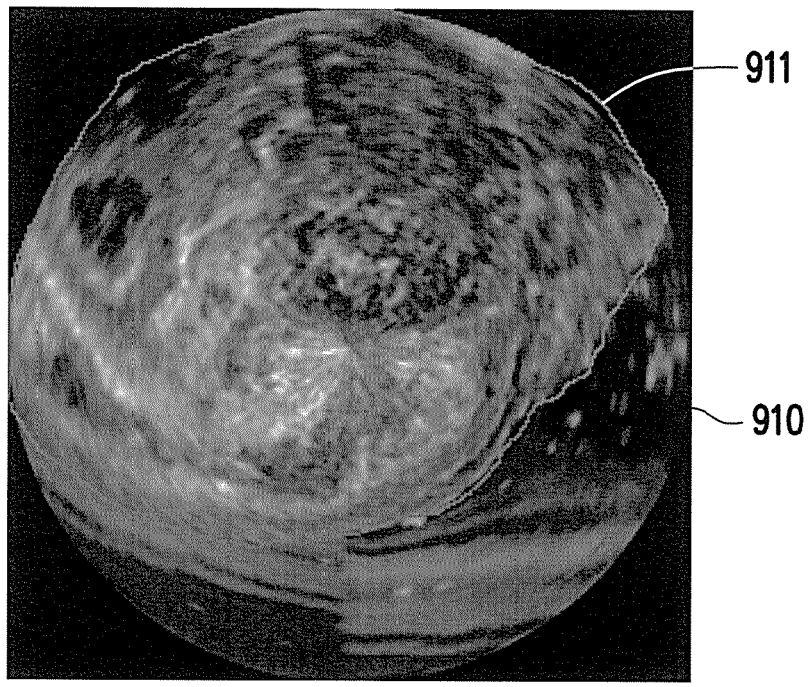
FIG. 9A is an example of a projection image.

The image quality module 117 may further remove an unnecessary region at the periphery of the skin tissue. For example, FIG. 9A is an example of a projection image. Referring to FIG. 9A, the image outside a target block 911 in the projection image 910 is considered to be the unnecessary region.

Figure 9B:
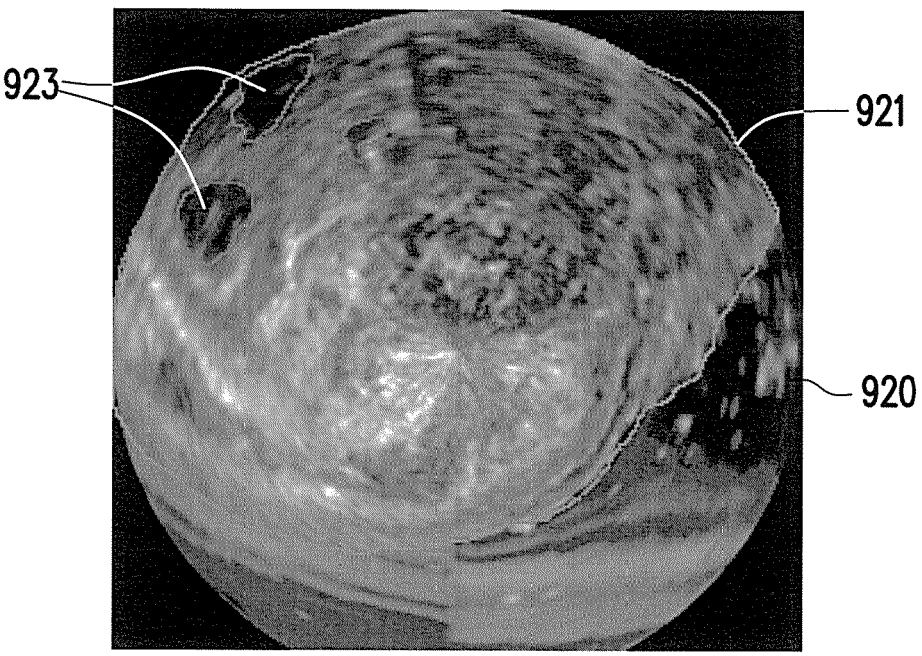
FIG. 9B is an example of a segmented projection image.

The image quality module 117 adopts the region segment method (for example, the watershed segment, MRF segment, etc.) to divide the projection image into a skin tissue type block and a shooting error type block according to the pixel characteristics of the target region. For example, FIG. 9B is an example of the segmented projection image. Referring to FIG. 9B, the segmented projection image 920 includes a skin tissue type block 921 and shooting error type blocks 923. The image quality module 117 may generate a ratio (for example, a total area of the shooting error type blocks 923 divided by a total area of the skin tissue type block 921) according to areas of the two types of blocks to determine a level of the image scanning quality. For example, if the ratio is greater than a quality threshold (for example, 30%, 20%, etc.), the image quality module 117 determines that the image scanning quality is poor, and the scanning operation is re-performed. For example, a prompt message "rescan is recommended!" is displayed through the display unit. Conversely, if the ratio is smaller than the quality threshold (for example, 15%, 30%, etc.), the image quality module 117 determines that the image scanning quality is good, and the lesion detection operation of the step S250 can be performed.

In summary, in the lesion detecting method and the lesion detecting apparatus for breast image in a rotating manner provided by the embodiments of the disclosure, the breast image in the rotating manner is reconstructed to facilitate the medical staff to inspect the same in different viewing directions. By using the region-based lesion detecting method, the lesion position can be screened, and can be compared with the 3D reconstructed breast image to reduce false-positive. Moreover, in the embodiment of the disclosure, the image scanning quality can be maintained though the image quality determination.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A lesion detecting method for breast image in a rotating manner, comprising:
    obtaining a set of breast image in the rotating manner, wherein the set of breast image in the rotating manner comprises a plurality of sub breast images;
    reconstructing the sub breast images to generate a reconstructed breast image; and
    comparing the reconstructed breast image with the set of breast image in the rotating manner without being reconstructed to confirm at least one lesion position, comprising:
        performing region segment to the set of breast image in the rotating manner without being reconstructed to generate a region segment image;
        determining at least one suspicious lesion region in the region segment image;
        performing a false-positive reduction operation to the at least one suspicious lesion region to determine the at least one lesion position; and
        determining whether a connected lesion region exists in the reconstructed breast image according to the at least one lesion position, so as to confirm the at least one lesion position.

2. The lesion detecting method for breast image in the rotating manner as claimed in claim 1, wherein before the step of obtaining the set of breast image in the rotating manner, the method further comprises:
    respectively obtaining the sub breast images through a scanner by circling under a breast image taking container for one circle to implement rotatory scanning.

3. The lesion detecting method for breast image in the rotating manner as claimed in claim 2, wherein the step of reconstructing the sub breast images comprises:
    transforming the sub breast images into an image set according to a scanning start position, a rotation angle and a rotation direction of the scanner;
    determining a missing position of a gap between each two adjacent sub breast images in the image set; and
    complementing the missing position through an interpolation method.

4. The lesion detecting method for breast image in the rotating manner as claimed in claim 1, wherein after the step of obtaining the set of breast image in the rotating manner, the method further comprises:
    performing vertical projection on an image of a partial thickness region in the set of breast image in the rotating manner to generate a projection image; and
    determining image quality of the set of breast image in the rotating manner according to a ratio between a shooting error type and a skin tissue type in the projection image.

5. A lesion detecting apparatus, comprising:
    a memory, storing a set of breast image in a rotating manner; and
    a processor, coupled to the memory, and configured to:
        obtain the set of breast image in the rotating manner, wherein the set of breast image in the rotating manner contains a plurality of sub breast images;
        reconstruct the sub breast images to generate a reconstructed breast image;
        compare the reconstructed breast image with the set of breast image in the rotating manner without being reconstructed to confirm at least one lesion position;
        perform region segment to the set of breast image in the rotating manner without being reconstructed to generate a region segment image;
        determine at least one suspicious lesion region in the region segment image, performs a false-positive reduction operation to the at least one suspicious lesion region to determine the at least one lesion position; and
        determine whether a connected lesion region exists in the reconstructed breast image according to the at least one lesion position, so as to confirm the at least one lesion position.

6. The lesion detecting apparatus as claimed in claim 5, wherein the sub breast images are respectively obtained through a scanner by circling under a breast image taking container for one circle to implement rotatory scanning.

7. The lesion detecting apparatus as claimed in claim 6, wherein the processor is further configured to:
    transform the sub breast images into an image set according to a scanning start position, a rotation angle and a rotation direction of the scanner;
    determine a missing position of a gap between each two adjacent sub breast images in the image set; and
    complement the missing position through an interpolation method.

8. The lesion detecting apparatus as claimed in claim 5, wherein the processor is further configured to:
    perform vertical projection on an image of a partial thickness region in the set of breast image in the rotating manner to generate a projection image; and
    determine image quality of the set of breast image in the rotating manner according to a ratio between a shooting error type and a skin tissue type in the projection image.

* * * * *